(12) United States Patent
Le et al.

(10) Patent No.: US 9,155,601 B2
(45) Date of Patent: Oct. 13, 2015

(54) PACKAGE OF ORAL CARE IMPLEMENTS

(75) Inventors: Yi Jun Le, Yangzhou (CN); Feng Zhi Zhang, Yangzhou (CN)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/110,017

(22) PCT Filed: Apr. 27, 2011

(86) PCT No.: PCT/CN2011/000718
§ 371 (c)(1),
(2), (4) Date: Oct. 4, 2013

(87) PCT Pub. No.: WO2012/145856
PCT Pub. Date: Nov. 1, 2012

(65) Prior Publication Data
US 2014/0021070 A1    Jan. 23, 2014

(51) Int. Cl.
*A61C 19/02*     (2006.01)
*B65D 71/50*     (2006.01)
*B65D 77/26*     (2006.01)
*A46B 15/00*     (2006.01)

(52) U.S. Cl.
CPC ............. *A61C 19/02* (2013.01); *A46B 15/0093* (2013.01); *B65D 71/50* (2013.01); *B65D 77/26* (2013.01); *A46B 2200/1066* (2013.01)

(58) Field of Classification Search
CPC .... B65D 73/0092; B65D 71/50; B65D 77/26; A46B 17/04; A46B 11/04; A46B 15/0093; A46B 2200/1066; A61C 19/02

USPC ............. 206/15.3, 361–362.3, 461–471, 806; 211/65
See application file for complete search history.

(56) References Cited

U.S. PATENT DOCUMENTS

| 1,180,056 | A | * | 4/1916 | Lundy ........................ 206/362.1 |
| 1,711,327 | A | * | 4/1929 | Rock .......................... 206/362.1 |
| D101,439 | S | * | 10/1936 | Doppelt ........................ D3/301 |
| 2,162,283 | A | * | 6/1939 | Oshman et al. ............ 206/362.3 |
| 2,418,615 | A | * | 4/1947 | Barna ........................ 206/362.1 |
| 2,471,979 | A | * | 5/1949 | Rozzi et al. ................ 206/362.1 |
| 2,484,157 | A | * | 10/1949 | Dunlap ...................... 206/362.1 |
| 2,642,331 | A | * | 6/1953 | Sprinkle .................... 206/362.1 |

(Continued)

FOREIGN PATENT DOCUMENTS

CN   201192165   2/2009
FR   2873103     1/2006

(Continued)

OTHER PUBLICATIONS

Preserve: Personal Care: Toothbrush in Mail Back Pack, http://www.preserveproducts.com/products/personalcare/toothbrush-mail-back-pack.html downloaded from the Internet on Mar. 2, 2011 1:09:26 PM, 1 p.

(Continued)

*Primary Examiner* — Bryon Gehman

(57) ABSTRACT

A package (1000) of oral care implements comprises an enclosure (100) having an internal cavity (110), a retainer (200), and a plurality of oral care implements (300) detachably mounted to the retainer (200) in a fixed orientation relative to one another. The retainer (200) and the oral care implements (300) are disposed within the internal cavity (110) of the enclosure (100).

16 Claims, 7 Drawing Sheets

(56) References Cited

U.S. PATENT DOCUMENTS

| | | | |
|---|---|---|---|
| 2,713,940 A | 7/1955 | Putnam et al. | |
| 2,950,946 A | 8/1960 | Starworth | |
| 3,220,543 A * | 11/1965 | McCord et al. | 206/362.2 |
| 4,362,174 A | 12/1982 | Baker et al. | |
| 4,854,457 A | 8/1989 | Perler | |
| 4,947,984 A | 8/1990 | Kaufman et al. | |
| 5,048,144 A | 9/1991 | Andrews | |
| 5,566,823 A | 10/1996 | Summers | |
| 6,726,011 B2 | 4/2004 | Sarkar et al. | |
| 7,143,462 B2 | 12/2006 | Hohlbein | |
| 7,306,098 B1 | 12/2007 | Rineer, Jr. | |
| 2001/0023837 A1* | 9/2001 | Brown | 206/362.1 |
| 2002/0121449 A1 | 9/2002 | Bowie | |
| 2003/0136694 A1 | 7/2003 | Fitzgibbons | |
| 2005/0109662 A1 | 5/2005 | Kirk | |
| 2005/0279663 A1* | 12/2005 | Citrigno | 206/362.1 |
| 2006/0076302 A1 | 4/2006 | Pretorius | |
| 2006/0169654 A1 | 8/2006 | Camacho-Pantoja | |
| 2007/0080081 A1 | 4/2007 | Chang | |
| 2009/0288972 A1 | 11/2009 | Kayser | |
| 2010/0051565 A1 | 3/2010 | Fonseca | |
| 2010/0200435 A1 | 8/2010 | Baus | |
| 2015/0129522 A1* | 5/2015 | Werden | A46B 17/08 |

FOREIGN PATENT DOCUMENTS

| | | |
|---|---|---|
| JP | 2001-39471 | 2/2001 |
| JP | 2002-2788 | 1/2002 |
| WO | WO 9517116 A1 * | 6/1995 |
| WO | WO 2007117254 A1 * | 10/2007 |

OTHER PUBLICATIONS

International Search Report issued in PCT/CN2011/000718 mailed Feb. 2, 2012.

* cited by examiner

US 9,155,601 B2

PACKAGE OF ORAL CARE IMPLEMENTS

CROSS-REFERENCE TO RELATED PATENT APPLICATIONS

The present application is a U.S. national stage application under 35 U.S.C. §371 of PCT Application No. PCT/CN2011/000718, filed Apr. 27, 2011. The disclosure of the above application is incorporated herein by reference.

FIELD OF THE INVENTION

The present invention relates generally to a package of oral care implements, and more specifically to a package of oral care implements having a cap that retains a plurality of oral care implements.

BACKGROUND OF THE INVENTION

In the oral care industry, efforts continue to be made to reduce the costs associated with packaging of oral care implements, such as toothbrushes. Oral care implements can be manufactured in a very cost-effective way, but the packaging can be expensive and lead to increased costs that must ultimately be paid for by the consumer. Oral care implements, such as toothbrushes, should be packaged in a manner that protects the tooth cleaning elements, such as bristles, against both physical damage and bacteria prior to use. Typically, oral care implements are individually packaged within a clamshell package that includes a backer card. Oftentimes, the backer card is a product information panel that is formed of a cardboard material. Thus, a significant amount of material is required to package just a single oral care implement. Furthermore, clamshell packages do not completely and adequately protect oral care implements against physical damage because a consumer can apply pressure to the clamshell package and cause splaying of the bristles. Thus, a need exists for an improved package for oral care implements that both protects the bristles against damage and is more cost-effective to manufacture.

BRIEF SUMMARY OF THE INVENTION

Exemplary embodiments of the invention are directed to a package of oral care implements. The package comprises an enclosure within which the oral care implements and a retainer are disposed. The retainer holds the oral care implements in a fixed orientation relative to one another.

In one embodiment, the invention can be a package of oral care implements comprising: an enclosure having an internal cavity; a retainer; and a plurality of oral care implements detachably mounted to the retainer in a fixed orientation relative to one another, the retainer and the oral care implements disposed within the internal cavity of the enclosure.

In another embodiment, the invention can be a package of toothbrushes comprising: a flexible bag having an internal cavity; a multi-cap comprising a housing forming a chamber having an open bottom end; and a plurality of toothbrushes each comprising a head and a handle, the head of each of the toothbrushes disposed within the chamber, the handle of each of the toothbrushes protruding from the open bottom end of the chamber, the multi-cap and the toothbrushes disposed within the internal cavity of the flexible bag.

In yet another embodiment, the invention can be a package of toothbrushes comprising: an enclosure having an internal cavity; a multi-cap comprising a housing forming a chamber having an open bottom end; and a plurality of toothbrushes each comprising a head and a handle, the head of each of the toothbrushes disposed within the chamber, the handle of each of the toothbrushes protruding from the open bottom end of the chamber, the multi-cap and the toothbrushes disposed within the internal cavity of the enclosure.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
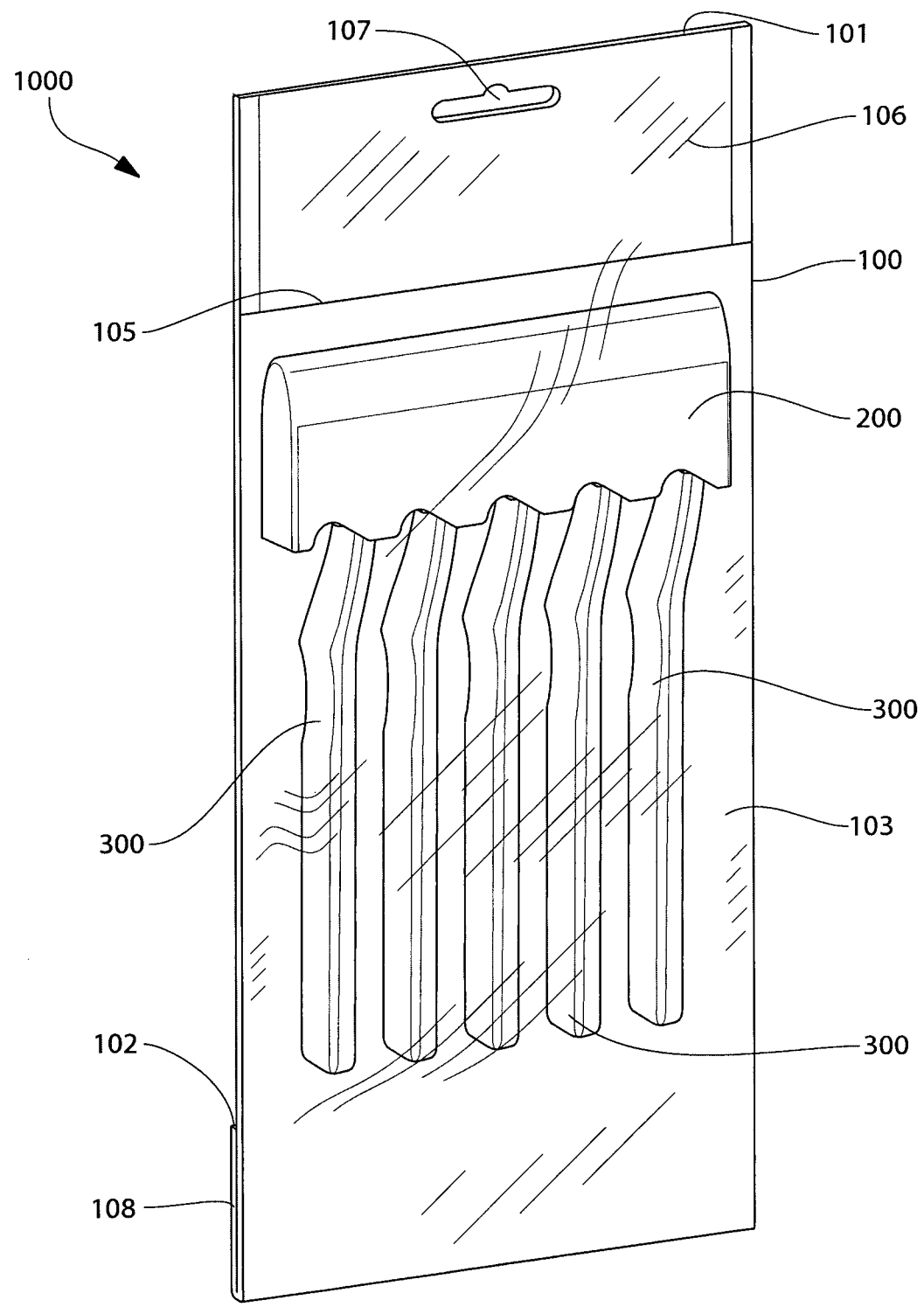
FIG. 1 is a front perspective view of a package of oral care implements according to an embodiment of the present invention, the package including a flexible bag and a retainer holding the oral care implements.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of the exemplary embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and similar refer to a relationship wherein structures are secured or attached to one another either directly or indirectly through intervening structures, as well as both movable or rigid attachments or relationships, unless expressly described otherwise. Moreover, the features and benefits of the invention are described by reference to the exemplary embodiments illustrated herein. Accordingly, the invention expressly should not be limited to such exemplary embodiments, even if indicated as being preferred. The discussion herein describes and illustrates some possible non-limiting combinations of features that may exist alone or in other combinations of features. The scope of the invention is defined by the claims appended hereto.

Figure 2:
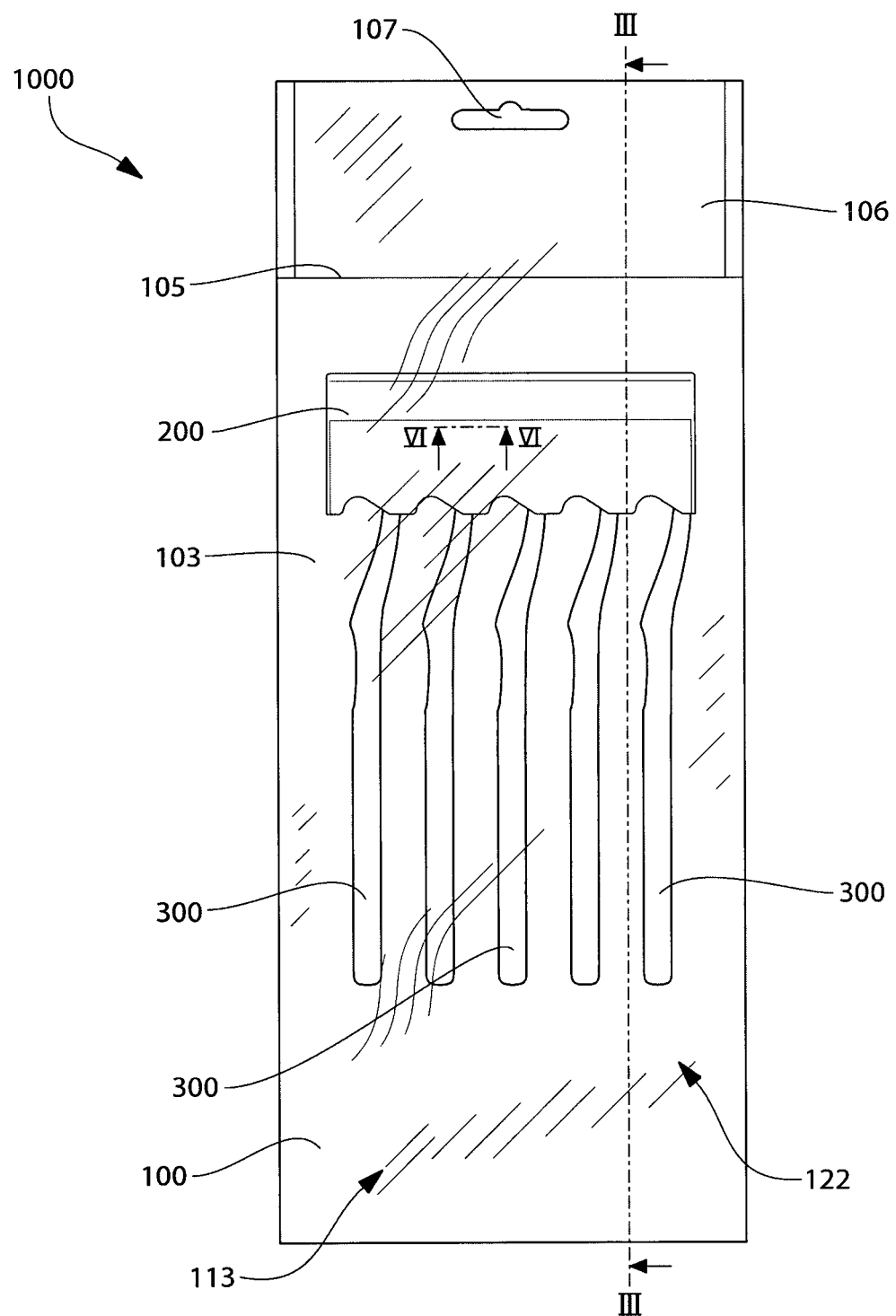
FIG. 2 is a front view of the package of oral care implements of FIG. 1.
Figure 3:
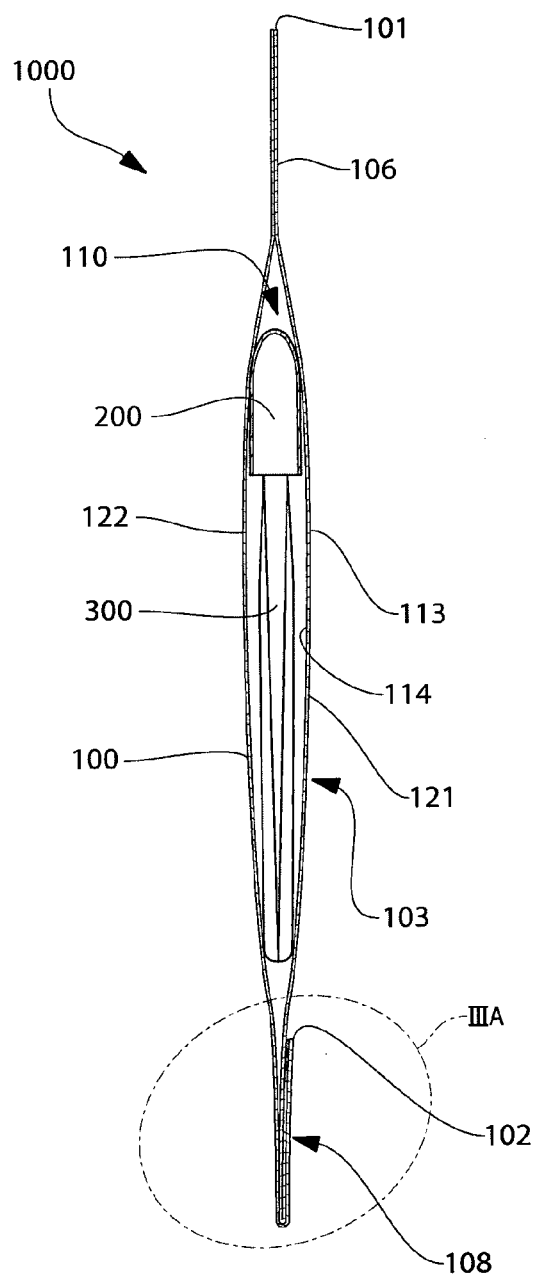
FIG. 3 is a longitudinal cross-sectional view of the package of FIG. 1 taken along line of FIG. 2.

Referring first to FIGS. 1-3 concurrently, a package of oral care implements 1000 is illustrated according to one embodiment of the present invention. The package 1000 generally comprises a flexible bag 100, a retainer 200 and a plurality of oral care implements 300. The flexible bag 100 is an enclosure within which the retainer 200 and the oral care implements 300 are disposed. The flexible bag 100 is preferably formed of a polymer-film such as, for example without limitation, high or low density polyethylene (HDPE and LDPE), coextruded polyethylene blends, polypropylene, nylon, polyester, embossed film or the like. Of course, the invention is not to be limited by the particular material used for constructing the flexible bag 100. However, it is preferable that the material forming the flexible bag 100 is impervious to fluids such that fluids can not penetrate the flexible bag 100 and damage the contents. In certain embodiments, the flexible bag 100 is formed of a film having a thickness in a range of 0.20 mm to 0.60 mm. In the exemplified embodiment, the flexible bag 100 is formed of a film having a thickness of approximately 0.40 mm plus tolerance. In certain embodiments, the package 1000 does not contain (i.e., is free of) a paperboard backer card and is free of any PVC thermoformed blister components, which helps to reduce manufacture costs.

In the exemplified embodiment, the flexible bag 100 is illustrated as a substantially rectangular shaped bag. Of course, the invention is not to be so limited and the flexible bag 100 may take on any other shape. Furthermore, at least a portion of the flexible bag 100 is preferably transparent so that the oral care implements 300 disposed therein can be viewed by a consumer at the point of sale. The flexible bag 100 is not limited to being completely transparent but may simply include clear windows. Furthermore, as used herein the term transparent is intended to include translucent materials or materials that are colored, yet capable of being seen through. Thus, in certain embodiments, such as the exemplified embodiment, the entire flexible bag 100 is formed of a transparent material. However, the invention is not so limited and in other embodiments, some portions of the flexible bag 100 are transparent and other portions are not transparent. Thus, in certain embodiments, the flexible bag 100 includes indicia such as logos, graphics, instructions, manufacturer information, advertising information, barcodes, product information or the like.

In the embodiment as shown, the flexible bag 100 forms a sleeve having a closed top end 101 and an open bottom end 102. As will be described in more detail below, a bottom portion 108 of the flexible bag 100, which includes the open bottom end 102, is folded upwardly and attached to a middle portion 103 of the flexible bag 100 so as to substantially enclose the flexible bag 100 for housing the retainer 200 and the oral care implements 300 therein and to prevent tampering. The flexible bag 100 further comprises a seal 105 that separates a top portion 106 of the flexible bag 100 from the middle portion 103 of the flexible bag 100. The top portion 106 of the flexible bag 100 comprises an aperture 107 to facilitate hanging of the package 1000 on a hook or peg in a retail store for display. Thus, in a retail store the flexible bag 100 can be hung from a hook, peg or other member that extends through the aperture 107. In other embodiments, flexible bag 100 may not include the aperture 107.

The flexible bag 100 comprises an inner surface 114 and an outer surface 113. The outer surface 113 of the flexible bag 100 comprises a front surface 122 and a rear surface 121. The inner surface 114 of the flexible bag 100 defines an internal cavity 110. When the package 1000 is fully assembled for retail sale, the oral care implements 300 are detachably mounted to the retainer 200 and the resulting assembly is disposed within the internal cavity 110 of the flexible bag 100. Once the assembly of the oral care implements 300 and the retainer 200 are positioned within the internal cavity 110 of the flexible bag 100, the flexible bag 100 is then closed as will be described below with reference to FIGS. 3 and 3A.

As described in greater detail below, when the oral care implements 300 are detachably mounted to the retainer 200, the retainer 200 does not completely enclose the oral care implements 300 (or seal the heads 310). Thus, if fluid penetrates the flexible bag 100 and enters the internal cavity 110, the fluid can contact the oral care implements 300, thereby potentially causing damage and/or contamination. Thus, in certain embodiments, in addition to the flexible bag 100 being formed of a material that is impervious to liquids, the entirety of the internal cavity 110 may be hermetically sealed by seam welding each of the edges of the flexible bag 100.

Figure 3A:
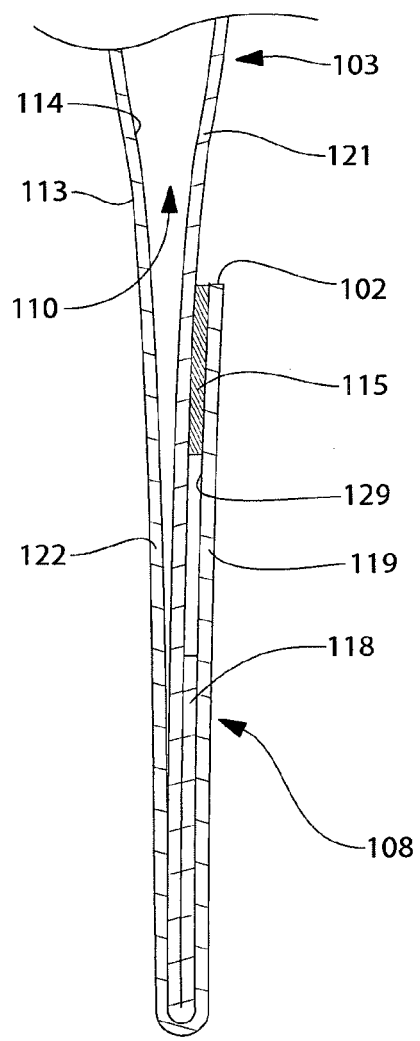
FIG. 3A is a close-up view of section IIIA of FIG. 3.

Referring now to FIGS. 3 and 3A concurrently, the open bottom end 102 can be sealed in a manner that allows repetitive opening and closing. As illustrated, the middle portion 103 is positioned between the top portion 106 of the flexible bag 100 and the bottom portion 108 of the flexible bag 100. The bottom portion 108 of the flexible bag 100 includes an inner layer 118 and an outer layer 119. The outer layer 119 extends beyond the inner layer 118. Thus, when the bottom portion 108, including the open bottom end 102 of the flexible bag 100 and the inner and outer layers 118, 119, is folded over the middle portion 103 of the flexible bag 100, the outer layer 119 extends further than does the inner layer 118.

An adhesive strip 115 is provided on an inner surface 129 of the outer layer 119 of the bottom portion 108 of the flexible bag 100. Thus, as the inner surface 129 of the outer layer 119 of the bottom portion 108 of the flexible bag 100 contacts the rear surface 121 of the middle portion 103 of the flexible bag 100, the adhesive strip 115 adheres to the rear surface 121 of the flexible bag 100, thereby becoming detachably secured thereto. In this way, the flexible bag 100 is secured in a closed position.

The adhesive strip 115 can be a strip of any type of adhesive material, including without limitation glue, double-sided tape or any other material known to bond items together. However, the adhesive strip 115 is preferably formed of a low-strength adhesive so that the bottom portion 108 can be repeatedly attached to and detached from the middle portion 103 of the flexible bag 100. Alternatively, the adhesive strip 115 may be hook and loop fasteners, snaps, buttons, zippers or any other mechanism that can be used to repeatedly open and close the flexible bag 100. As such, the oral care implements 300 disposed within the internal cavity 110 of the flexible bag 100 can be removed from the flexible bag 100 one by one over extended period of time as needed. Each time one of the oral care implements 300 is removed from or replaced into the internal cavity 110, the flexible bag 100 can be put into the closed position by folding the bottom portion 108 over the middle portion 103 and contacting the adhesive strip 115 to the rear surface 121 of the middle portion 103 of the flexible bag 100.

Figure 4:
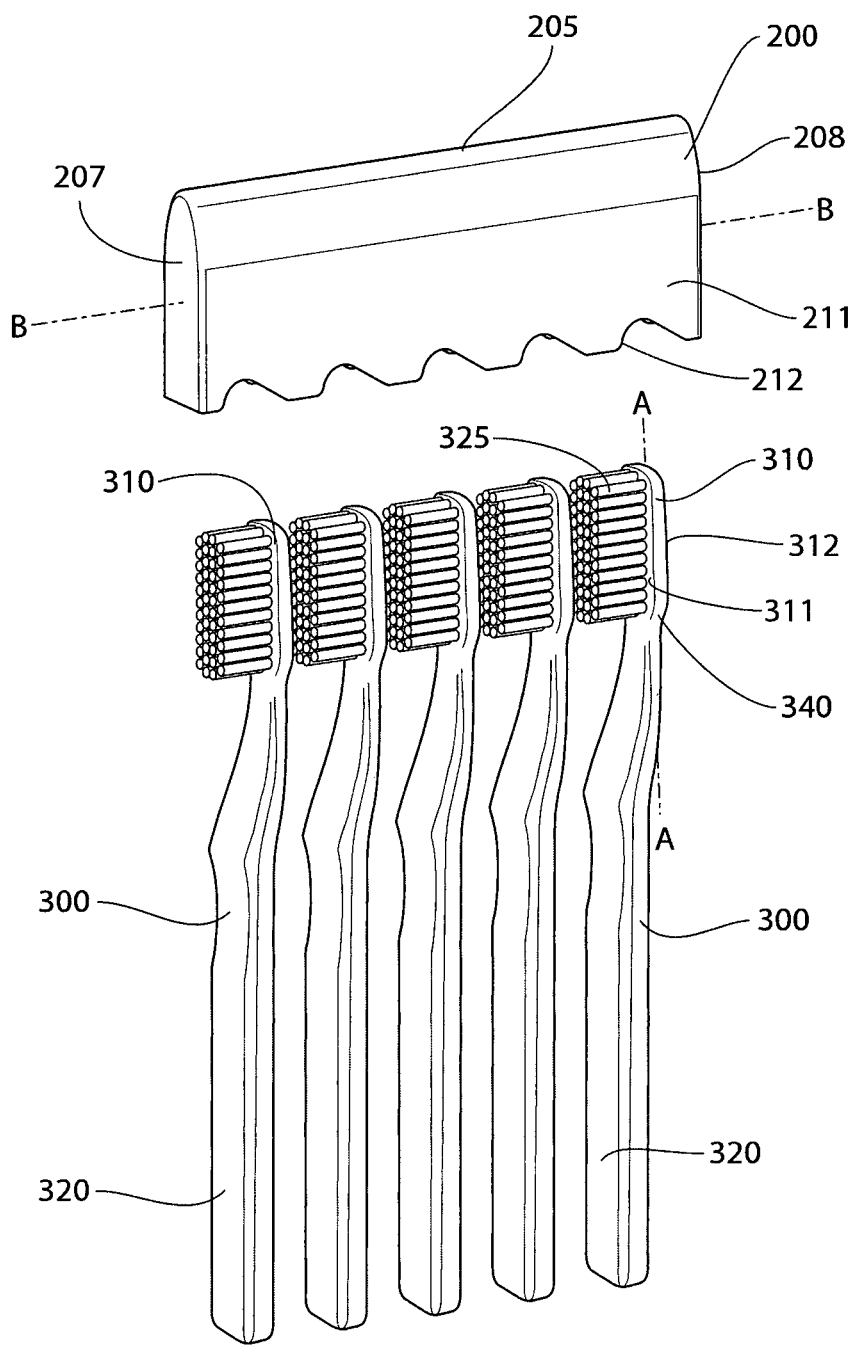
FIG. 4 is front perspective view of the oral care implements and the retainer of FIG. 1 removed from the flexible bag, wherein the oral care implements are detached from the retainer.

Referring to FIG. 4, a plurality of the oral care implements 300 are illustrated according to one embodiment of the present invention. The oral care implements 300 are detached from the retainer 200. In the exemplified embodiment, the oral care implements 300 are shown as manual toothbrushes. However, the invention is not so limited in all embodiments and, in other embodiments, the oral care implement 300 can take the form of powered toothbrushes, interdental devices, tongue scrapers, soft tissue cleansers or the like.

Each one of the plurality of oral care implements 300 comprises a head 310 and a handle 320. Each of the heads 310 of the oral care implements 300 extend from a distal end of the handle 310 along a longitudinal axis A-A. In the exemplified embodiment, the oral care implements 300 are generically illustrated. However, the oral care implements 300 can take on any of a wide variety configurations and shapes, and include additional components and/or capabilities. For example, each of the heads 310 of the oral care implements 300 can have surfaces that are planar, contoured or combinations thereof. Each of the oral care implements 300 is constructed of a material having suitable rigidity for handling of the oral care implement 300. Suitable materials for the oral care implements 300 include hard plastics, such as polyethylene, polypropylene (PP), polyamide, polyester, cellulosics, SAN, acrylic, ABS or any other of the commonly known thermoplastics used in toothbrush manufacture.

The handles 320 of the oral care implements 300 may include an elastomeric material, such as a thermoplastic elastomer, to enhance comfort to a user when the user is handling the oral care implement 300. In the exemplary embodiment, the head 310 and the handle 320 are integrally formed as a single unitary structure using a molding, milling, machining or other suitable process. However, in other embodiments the handle 320 and the head 310 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Whether the head 310 and the handle 320 are of a unitary or multi-piece construction (including connection techniques) is not limiting of the present invention, unless specifically claimed. In some embodiments of the invention, the head 310 may be detachable (and replaceable) from the handle 320 using techniques known in the art.

The head 310 comprises a front surface 311 and an opposing rear surface 312. The rear surface 312 of the head 310 may comprise a soft tissue cleanser, which may be in the form of protuberances on the rear surface 312 of the head 310 or may be an attached elastomeric element. An example of a suitable elastomeric soft tissue cleanser that may be used with the present invention and positioned on the rear surface 312 of the head 310 is disclosed in U.S. Pat. No. 7,143,462, issued Dec. 5, 2006 to the assignee of the present application, the entirety of which is hereby incorporated by reference.

The front surface 311 of the head 310 comprises a plurality of tooth cleaning elements 325 extending outwardly therefrom. The tooth cleaning elements 325 are generically illustrated as a plurality of tufts of bristles. However, the invention is in no way limited by the configuration or material of the tooth cleaning elements 325. Furthermore, while the plurality of tooth cleaning elements 325 are particularly suited for brushing and/or polishing teeth, the plurality of tooth cleaning elements 325 can also be used to clean oral soft tissue, such as a tongue, gums, or cheeks instead of or in addition to teeth. As used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of tooth cleaning elements include, without limitation, bristle tufts, filament bristles, fiber bristles, nylon bristles, spiral bristles, rubber bristles, elastomeric protrusions, flexible polymer protrusions, combinations thereof and/or structures containing such materials or combinations.

Figure 5:
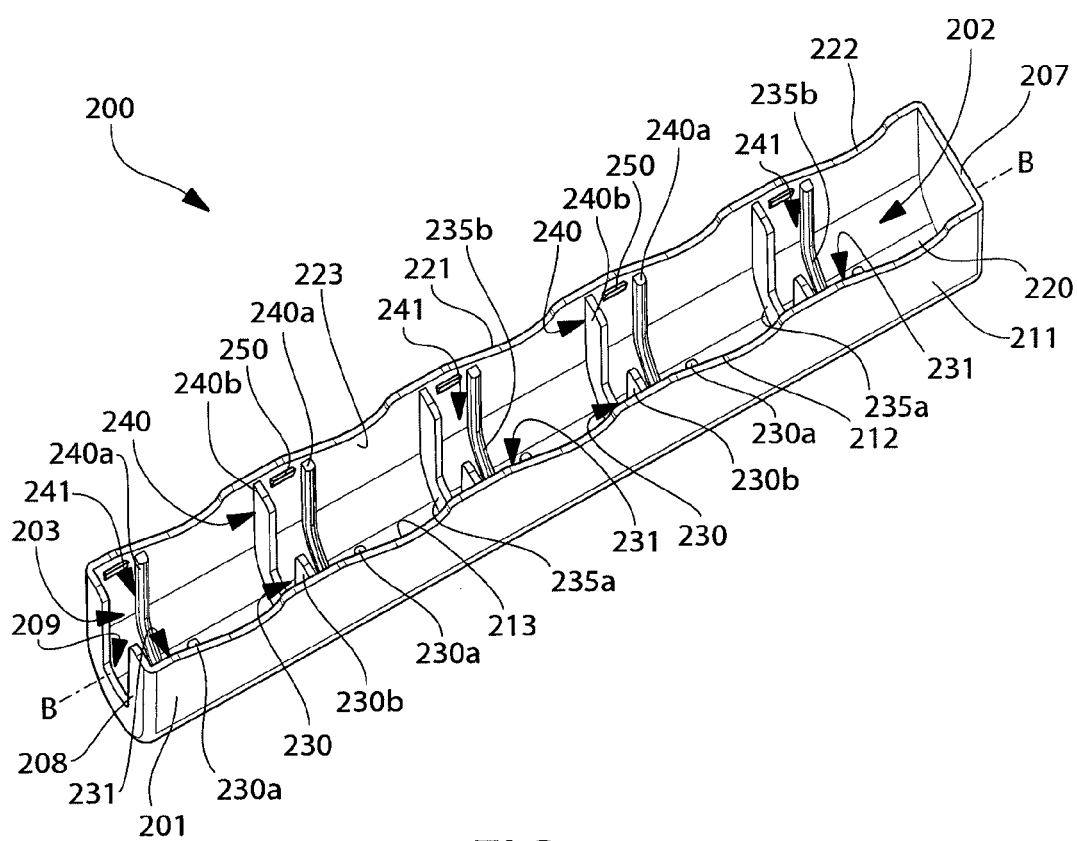
FIG. 5 is a bottom perspective view of the retainer of FIG. 1.

Referring now to FIGS. 4 and 5 concurrently, the retainer 200 will be described in greater detail. The retainer 200 is formed of a hard plastic material in one embodiment. Suitable hard plastic materials include and of the material described above for the oral care implements 300. Of course, the invention is not so limited and the retainer 200 can be formed of other materials, including metal, wood, or any other sufficiently rigid or hard material. The retainer 200 is preferably formed of a material and with sufficient structural stability so that it can protect the heads 310 of the oral care implements 300, and more particularly the tooth cleaning elements 325, contained therein against physical damage. Thus, the retainer 200, in certain embodiments, is sufficiently rigid so as to allow a consumer to grip and squeeze the retainer 200 without causing the retainer 200 to substantially collapse and damage the tooth cleaning elements 325. Of course, the retainer 200 will be capable of some degree of collapse and/or deformation under excessive force. Furthermore, when the oral care implements 300 are detachably mounted to the retainer 200, the resulting assembly becomes more rigid and difficult to compress because the heads 310 of the oral care implements 300, which are formed of a hard plastic material, are disposed within the retainer 200 so as to conceptually act as struts.

The retainer 200 comprises an elongated housing 201 that forms a chamber 202. The housing 201 comprises a first sidewall 207 to a second sidewall 208 and extends along a longitudinal axis B-B. The retainer 200 further comprises an elongated slot 203 that forms a passageway into the chamber 202. As a result, the retainer 200 has an open bottom end. As will be described below with reference to FIGS. 6-8, the oral care implements 300 are detachably mounted to the retainer 200 such that the heads 310 of the oral care implements 300 are disposed within the chamber 202 and the handles 320 of the oral care implements 300 protrude from the slot 203 or the open bottom end of the retainer 200. Thus, in certain embodiments, such as the one exemplified, the retainer 200 is a multi-cap because it forms a cover or cap for a plurality of the oral care implements 300. In other embodiments, the retainer 200 may not cover or form a cap for the heads 310 of the oral care implements 300. Moreover, while in the exemplified embodiment the heads 310 of the oral care implements 300 are fully disposed within the chamber 202, the heads 310 of the oral care implements 300 may be only partially disposed within the chamber 202 in other embodiments.

The housing 201 of the retainer 200 comprises a first wall 211 and a second wall 221 opposite the first wall 211. The first wall 211 has a bottom edge 212 and the second wall 221 has a bottom edge 222. In the exemplified embodiment, the bottom edges 212, 222 of each of the first and second walls 211, 221 have an undulated contour. In certain other embodiments, however, the bottom edges 212, 222 of the first and second walls 211, 221 can be straight edges or comprises a single continuous contour. The bottom edges 212, 222 may take on any shape, as desired. The slot 203 (which forms a passageway into the chamber 202) is formed between the bottom edge 212 of the first wall 211 and the bottom edge 222 of the second wall 221. The slot 203 extends along the longitudinal axis B-B of the housing 201 from the first sidewall 207 to the second sidewall 208. In the exemplified embodiment, the slot 203 is a continuous aperture. However, in certain other embodiments, the slot 203 may be formed by a plurality of aperture segments that are separated by walls that extend between the bottom edges 212, 222 of the first and second walls 211, 221. It should be understood that whether the retainer 200 comprises a continuous slot or a segment slot, the resulting aperture(s) should be large enough to enable the heads 310 of the oral care implements 300, including the tooth cleaning elements 325, to pass therethrough and into the chamber 202.

The first and second walls 211, 221 converge towards each other as they extend away from their bottom edges 212, 222, thereby forming a domed roof portion 205. Thus, the housing 201 of the retainer 200 has a generally U-shaped transverse cross-sectional profile. In certain embodiments, the shape of the chamber 202 of the housing 201 corresponds with the shape of the heads 310 of the oral care implements 300 that are to be positioned therein. For example, in some embodiments, the housing 201 may have a generally V-shaped transverse cross-sectional profile, a generally trapezoidal transverse cross-sectional profile, or a generally rectangular transverse cross-sectional profile, etc. As mentioned above, the housing 201 also comprises the first sidewall 207 and the second sidewall 208 that enclose the opposing ends of the housing 201. In the exemplified embodiment, the second sidewall 208 comprises an opening 209 therethrough. However, in certain other embodiments the first and second sidewalls 207, 208 may each have an opening or the opening 209 may be omitted altogether.

The first wall 211 comprises an inner surface 213 and the second wall 221 comprises an inner surface 223. The inner surface 213 of the first wall 211 is connected to the inner surface 223 of the second wall 221 by an inner surface 220 of the domed roof 205 of the housing 201. The housing 201 comprises a plurality of pairs of ribs 230 protruding outwardly from the inner surface 213 of the first wall 211 and into the chamber 202 and a plurality of pairs of ribs 240 extending outwardly from the inner surface 223 of the second wall 221 and into the chamber 202. Each of the pairs of ribs 230 comprises a first rib 230a and a second rib 230b and each of the pairs of ribs 240 comprises a first rib 240a and a second rib 240b. As will be described in more detail below, the first ribs 230a, 240a extend a smaller distance into the chamber 202 than the second ribs 230b, 240b. It should be understood that less than all of the pairs of ribs 230, 240 are labeled in FIG. 5 to avoid clutter. While the first and second ribs 230a, 230b, 240a, 240b are illustrated to extend outwardly from the entirety of inner surfaces 213, 223, in some embodiments, the first and second ribs 230a, 230b, 240a, 240b are illustrated to extend outwardly from a portion of inner surfaces 213, 223.

In the exemplified embodiment, there are five pairs of ribs 230 and five pairs of ribs 240. Thus, the exemplified retainer 200 is designed to have five of the oral care implements 300 detachably mounted thereto. In other embodiments, the retainer 200 may be designed or configured to contain more or less than five of the oral care implements 300 but preferably at least two.

Figure 6:
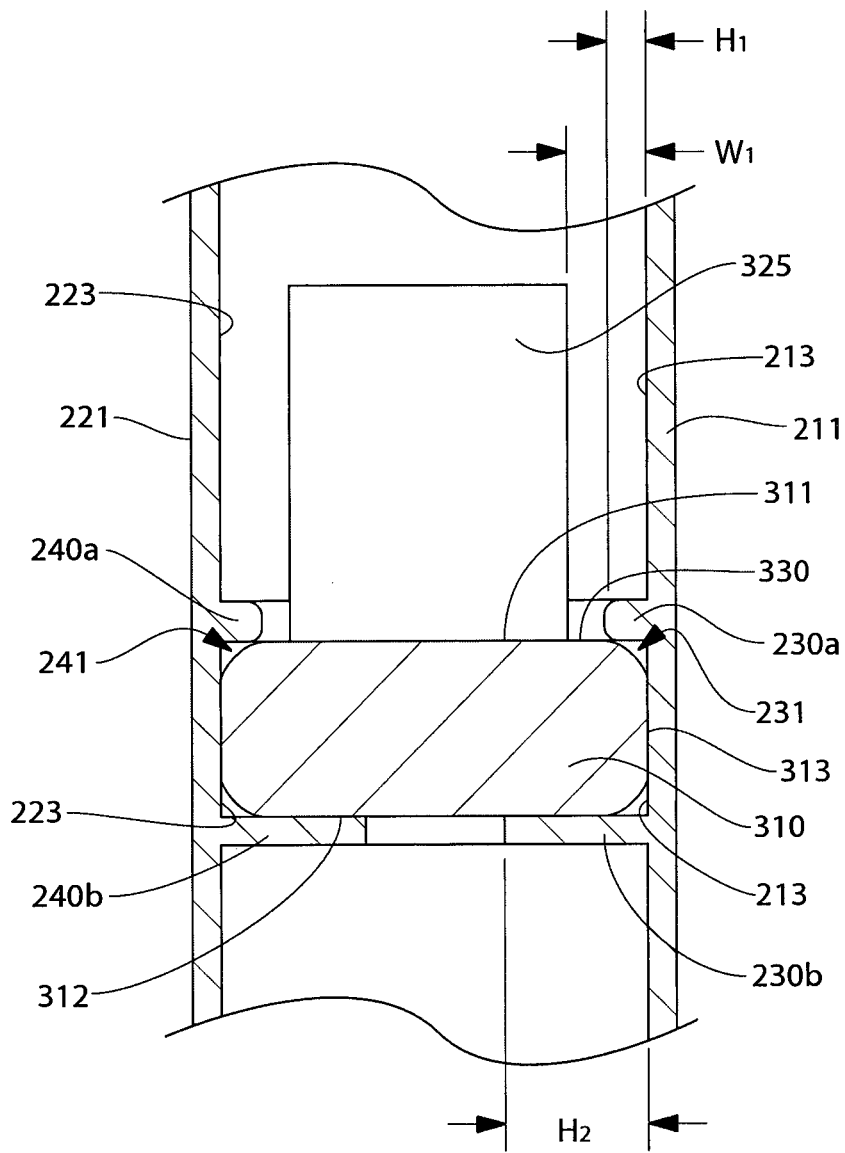
FIG. 6 is a cross-sectional view of the package of oral care implements of FIG. 1 taken along line VI-VI of FIG. 2, wherein the flexible bag is omitted.

Referring now to FIGS. 5 and 6 concurrently, the retainer 200, including its structural cooperation with the oral care implements 300, will be described in greater detail. Each of the pairs of ribs 230 forms a receiving channel 231 between the first rib 230a and the second rib 230b on the inner surface 213 of the first wall 211. Similarly, each of the pairs of ribs 240 forms a receiving channel 241 between the first rib 240a and the second rib 240b on the inner surface 223 of the second wall 221. Each one of the receiving channels 231 has a corresponding receiving channel 241 with which it is longitudinally aligned. The receiving channels 231, 241 are sized and shaped so that the heads 310 of the oral care implements 300 can be nested therein. In one embodiment, the appropriate dimensions of the retainer 200 and the oral care implements 300 are selected so that the heads 310 of the oral care implements 300 preferably are detachably retained within the chamber 202 by an interference fit, such that the front surfaces 311 of the heads 310 are in sliding contact with the first ribs 230a, 240a and the rear surfaces 312 of the heads 310 are in sliding contact with the second ribs 230b, 240b.

In the exemplified embodiment, each one of the ribs is a U-shaped rib such that the first rib 230a forms a first leg of the "U" and the first rib 240a forms a second leg of the "U," thereby collectively forming a single U-shaped rib. Similarly, in the exemplified embodiment the second rib 230b forms a first leg of another "U" and the second rib 240b forms a second leg of the another "U." In such an embodiment, the first rib 230a is connected to the first rib 240a by a bight portion 235a that extends from the inner surface 220 of the domed roof 205 of the housing 201 and the second rib 230b is connected to the second rib 240b by a bight portion 235b that extends from the inner surface 220 of the domed rood 205 of the housing 201. Thus, in the exemplified embodiment, each of the receiving channels 231, 241 is a single continuous channel extending along the entirety of the interior surface (including inner surfaces 213, 223 and inner surface 220) of the housing 201. In certain other embodiments, however, the bight portions 235a, 235b may be omitted. In such an embodiment, the pairs of ribs 230, 240 can simply be formed by the first and second ribs 230a, 230b that protrude into the chamber 202 from the inner surface 213 of the first wall 211 and the first and second ribs 240a, 240b that protrude into the chamber 202 from the inner surface 223 of the second wall 221, respectively. In such an embodiment, the channels 231, 241 are separated from each other and positioned directly opposite each other, each being formed in its respective sidewall 211, 221.

In the exemplified embodiment, one of the second ribs 230b, 240b is formed by the second sidewall 208. Thus, one of the receiving channels 231 is formed between the second sidewall 208 and one of the first ribs 230a and a corresponding one of the receiving channels 241 is formed between the second sidewall 208 and one of the first ribs 240a. The opening 209 in the second sidewall 208 enables the oral care implement 300 disposed in the channel 231, 241 between the second sidewall 208 and the first ribs 230a, 240a to fit therein even if the head 310 of the oral care implement 300 comprises a soft tissue cleanser or other protuberance on its rear surface 312.

The housing 201 of the retainer 200 further comprises a retaining tab 250 protruding from each of the inner surfaces 213, 223 of the first and second walls 211, 221. Specifically, the retaining tabs 250 protrude from the inner surfaces 213, 223 of the first and second walls 211, 221 into the receiving channels 231, 241 of each pair of ribs 230, 240. The retaining tabs 250 engage shoulder portions 340 (FIG. 4) of each of the heads 310 of the oral care implements 300 when the oral care implements 300 are detachably mounted within the chamber 202. Thus, the retaining tabs 250 prevent the heads 310 of the oral care implements 300 from being dislodged from the chamber 202 inadvertently, and more specifically from the receiving channels 231, 241. However, it is preferable that the retaining tabs 250 be small projections so that excessive force is not required to detach the oral car implements 300 from the retainer 200. The retaining tabs 250 should be small enough so that a user can easily remove any one of the oral care implements 300 from the retainer 200 by gently pulling either the oral care implements 300 or the retainer 200 away from the other. In some embodiments, the receiving channels 231, 241 may be sized appropriately such that the retaining tabs 250 are not included in the retainer 200.

Referring solely now to FIG. 6, one of the oral care implements 300 is illustrated positioned within the receiving channels 231, 241. Specifically, the head 310 of the oral care implement 300 is positioned within the retainer 200 such that the head 310 is nested within one of the receiving channels 231 on the first wall 211 and one of the receiving channels 241 on the second wall 221. Each one of the receiving channels 231 on the first wall 211 has a corresponding receiving channel 241 on the opposing second wall 221 that is positioned at the same location along the longitudinal axis B-B. Thus, each one of the oral care implements 300 is nested within one of the receiving channels 231 on the first wall 211 and its corresponding receiving channel 241 on the second wall 221.

The front surface 311 of the head 310 of the oral care implement 300 comprises a peripheral portion 330. The peripheral portion 330 is a portion of the front surface 311 of the head 310 that is free of the tooth cleaning elements 325. In other words, there are no tooth cleaning elements 325 extending from the peripheral portion 330 of the front surface 311 of the head 310. The peripheral portion 330 of each of the oral care implements 300 comprises a width W1 that that extends from the tooth cleaning elements 325 to a side wall 313 of the head 310 of the oral care implement 300.

Each one of the first ribs 230a, 240a extends from the inner surface 213, 223 of its respective sidewall 211, 221 a first height H1. The first height H1 is less than or equal to the width W1 of the peripheral portion 330 of the head 310 of the oral care implement 300. Furthermore, each one of the second ribs 230b, 240b extends from the inner surface 213, 223 of its respective sidewall 211, 221 a second height H2. In the exemplified embodiment, the second height H2 is greater than each of the first height H1 and the width W1 of the peripheral portion 330 of the head 310 of the oral care implement 300. Thus, the oral care implements 300 must be disposed within the channels 231, 241 so that the first ribs 230a, 240a are adjacent the front surface 311 of the head 310 and the second ribs 230b, 240b are adjacent the rear surface 312 of the head 310. If the oral care implements 300 are otherwise positioned within the channels 231, 241, the second ribs 230b, 240b will contact the tooth cleaning elements 325 as the oral care implements 300 are being slid into the channels 231, 241, thereby causing damage to or splaying of the tooth cleaning elements 325.

As can be seen in FIG. 6, when the oral care implements 300 are positioned within the channels 231, 241 of the retainer 200, the heads 310 of the oral care implements 300 extend between the first and second sidewalls 211, 221 and the peripheral portions 330 of the heads 310 of the oral care implements 300 are nested within the receiving channel 231 on the first wall 211 and the corresponding receiving channel 241 on the second wall 221. Furthermore, the heads 310, and more specifically the side walls 313 of the heads 310 of the oral care implements 300 are in contact with both the first and second sidewalls 211, 221 of the housing 201 of the retainer 200. Additionally, when the oral care implements 300 are properly positioned within the channels 231, 241 of the retainer 200, the tooth cleaning elements 325 do not come into contact with any portion of the retainer 200 or with any of the other oral care implements 300. As such, the tooth cleaning elements 325 can be protected against damage when the heads 310 of the oral care implements 300 are disposed within the retainer 200.

Figures 7, 8:
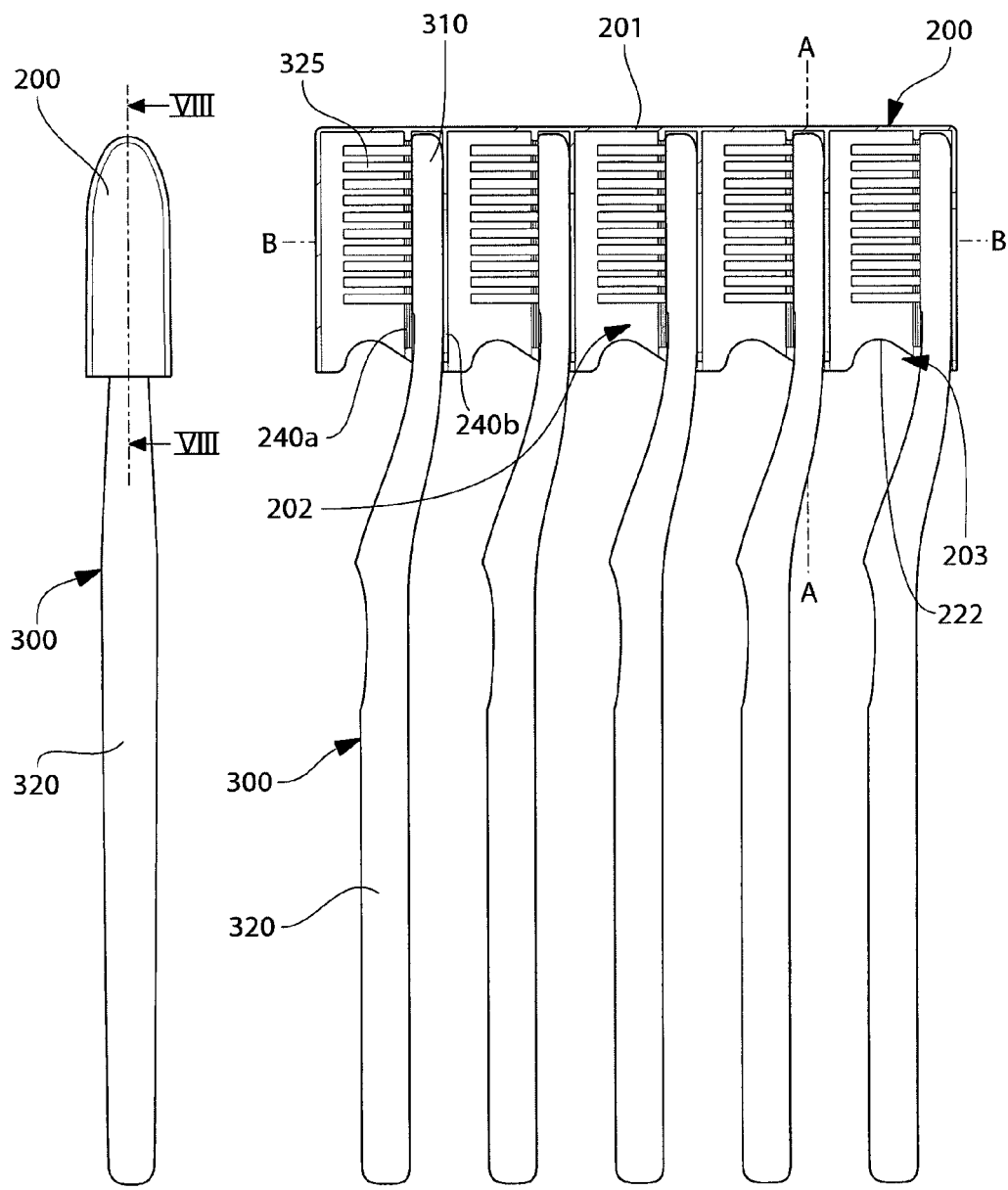
FIG. 7 is a side view of the oral care implements and the retainer of FIG. 1 removed from the flexible bag, wherein the oral care implements are detachably mounted to the retainer.
FIG. 8 is a longitudinal cross-sectional view of the oral care implements and the retainer of FIG. 7 taken along line VIII-VIII of FIG. 7.

Referring now to FIGS. 7 and 8, the retainer 200 is illustrated with a plurality of the oral care implements 300 mounted thereto. As discussed, above, in the exemplified embodiment the retainer 200 is sized and configured to contain five of the oral care implements 300 therein. However, the invention is not limited by the particular number of oral care implements 300 that can be detachably mounted to the retainer 200. When a plurality of the oral care implements 300 are mounted to the retainer 200, the oral care implements 300 are in a fixed orientation relative to one another such that the handles 320 of the oral care implements 300 are substantially parallel to one another. Due to the interference fit and the retaining tabs 250 discussed above, the oral care implements 300 remain in a fixed orientation while being mounted to the retainer 200. Furthermore, when the oral care implements 300 are properly mounted to the retainer 200, the heads 310 of the oral care implements 300 are disposed within the chamber 202 and the handles 320 of the oral care implements 300 protrude from the slot 203.

As discussed above, each of the heads 310 of the oral care implements 300 comprises the longitudinal axis A-A. Furthermore, the housing 201 of the retainer 200 comprises the longitudinal axis B-B. The longitudinal axes A-A of the heads 310 of the oral care implements 300 are substantially perpendicular to the longitudinal axis B-B of the housing 201 of the retainer 200. Due to the fixed orientation with which the oral care implements 300 are mounted to the retainer 200, the tooth cleaning elements 325 of each of the oral care implements 300 do not contact any portion of any of the other oral care implements 300. This mounting of the oral care implements 300 to the retainer 200 further protects the tooth cleaning elements 325 of each of the oral care implements 300 against damage or other degradation prior to use.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments. For example, in certain embodiments, the delivery of the oral care fluid from the reservoir to the applicator can be supplemented by mechanical action if desired.

What is claimed is:

1. A package of toothbrushes comprising:
a flexible bag having an internal cavity;
a multi-cap, comprising;
   a housing forming a chamber having an open bottom end;
   a plurality of first ribs disposed within the chamber, wherein each first rib comprises a first leg and a second leg, and the first leg and the second leg of each of the plurality of first ribs define a first opening therebetween;
   a plurality of second ribs disposed within the chamber, wherein each second rib comprises a first leg and a second leg, and the first leg and the second leg of each of the plurality of second ribs define a second opening therebetween;
   wherein each first rib is paired with one of the second ribs from the plurality of second ribs;
   a plurality of receiving channels defined within the chamber, wherein each receiving channel of the plurality of receiving channels is defined by one pair of the paired first ribs and second ribs; and
a plurality of toothbrushes each comprising a head and a handle, the head of each of the toothbrushes disposed within the chamber and within one of the receiving channels, the handle of each of the toothbrushes protruding from the open bottom end of the chamber, the multi-cap and the toothbrushes disposed within the internal cavity of the flexible bag.

2. The package according to claim 1 wherein the heads of the toothbrush are disposed within the chamber so as to detachably mount the toothbrushes to the multi-cap in a fixed orientation relative to one another.

3. The package according to claim 2 wherein the handles of the toothbrushes are substantially parallel to one another.

4. The package according to claim 1 wherein the toothbrushes are detachably mounted to the multi-cap via an interference fit between the heads of the toothbrushes and the housing of the multi-cap.

5. The package according to claim 1 wherein the housing comprises a first wall having an inner surface and a second wall opposite the first wall and having an inner surface, the first leg of each of the plurality of first ribs and the first leg of each of the plurality of second ribs are attached to the inner surface of the first wall, the second leg of each of the plurality of first ribs and the second leg of each of the plurality of second ribs are attached to the inner surface of the second wall, each first leg and second leg protrudes into the chamber, each paired first rib and second rib forming a receiving channel, each of the heads of the toothbrushes nesting in one of the receiving channels on the first wall and another one of the receiving channels on the second wall.

6. The package according to claim 5 wherein the housing comprises a retaining tab protruding into each of the receiving channels, the retaining tabs engaging shoulder portions of the heads of the toothbrushes.

7. The package according 5 wherein each paired first rib and second rib comprises a U-shaped rib having a bight portion extending from a roof of the housing and between one of the first legs and one of the second legs.

8. The package according to claim 1 wherein each of the heads of the toothbrushes comprises a longitudinal axis and the housing of the multi-cap comprises a longitudinal axis, and wherein the longitudinal axes of the heads are substantially perpendicular to the longitudinal axis of the housing of the multi-cap.

9. The package according to claim 1 wherein the multi-cap is constructed of a hard plastic.

10. The package according to claim 1 wherein the flexible bag is constructed of a polymer-film.

11. The package according to claim 1 comprising at least three of the toothbrushes.

12. The package according to claim 1 wherein the housing comprises a first wall and a second wall opposite the first wall, the heads of the toothbrushes extending between and in contact with the first and second walls.

13. The package according claim 12 wherein each of the heads of the toothbrushes comprises a peripheral portion free of tooth cleaning elements, the peripheral portion having a width, wherein each first rib has a height that is less than or equal to the width of the peripheral portion.

14. The package according to claim 1 wherein each of the toothbrushes comprises a plurality of tooth cleaning elements mounted to the head, and wherein the tooth cleaning elements of each of the toothbrushes pass through one of the first openings and do not contact any portion of the multi-cap or any portion of any of the other toothbrushes.

15. The package according to claim 1, wherein the chamber comprises each opening defined by the first leg and the second leg of each of the plurality of first ribs and second ribs.

16. The package according to claim 1, wherein each first opening and each second opening is continuous with all remaining first and second openings.

* * * * *